United States Patent
Fisset et al.

(10) Patent No.: US 9,976,964 B2
(45) Date of Patent: May 22, 2018

(54) METHOD OF MEASURING A PARAMETER OF A COMPOSITE MOULDING MATERIAL

(71) Applicant: Hexcel Composites Limited, Duxford (GB)

(72) Inventors: Emilie Fisset, Duxford (GB); John Ellis, Duxford (GB); Stuart Munday, Duxford (GB)

(73) Assignee: Hexcel Composites Limited, Duxford (GB)

( * ) Notice: Subject to any disclaimer, the term of this patent is extended or adjusted under 35 U.S.C. 154(b) by 170 days.

(21) Appl. No.: 15/035,962

(22) PCT Filed: Nov. 20, 2014

(86) PCT No.: PCT/EP2014/075201
§ 371 (c)(1),
(2) Date: May 11, 2016

(87) PCT Pub. No.: WO2015/075147
PCT Pub. Date: May 28, 2015

(65) Prior Publication Data
US 2016/0299085 A1    Oct. 13, 2016

(30) Foreign Application Priority Data
Nov. 22, 2013   (GB) .................................. 1320650.3

(51) Int. Cl.
*B29C 70/10*    (2006.01)
*G01N 21/86*    (2006.01)
(Continued)

(52) U.S. Cl.
CPC ............. *G01N 21/86* (2013.01); *B29C 66/45* (2013.01); *B29C 70/16* (2013.01); *G01N 23/16* (2013.01);
(Continued)

(58) Field of Classification Search
CPC ..... B29C 66/45; B29C 70/16; B29K 2101/12; B29K 2105/0872; B29K 2307/04;
(Continued)

(56) References Cited

U.S. PATENT DOCUMENTS 4,575,634 A    3/1986   Redler et al.
9,675,990 B2*  6/2017   Ellis ....................... G01N 27/90
(Continued)

FOREIGN PATENT DOCUMENTS

WO    2013/093071    6/2013

OTHER PUBLICATIONS

Robert C. et al.: "Dual-Energy Computed Tomography for Ceramics and Composite Materials", in "Review of Progress in Quantitative Nondestructive Evaluation" 1996—vol. 15, pp. 481-488.

*Primary Examiner* — George Koch
(74) *Attorney, Agent, or Firm* — W. Mark Bielawski; David J. Oldenkamp

(57) ABSTRACT

A method of controlling a process for the manufacture of a multicomponent sheet material having a desired pre-determined parameter comprising applying electromagnetic energy to interact with the sheet material whereby the interaction modifies the applied energy, detecting the modified energy, comparing the modified energy or data derived from it with data relating to the pre-determined parameter and modifying at least one step of the process whereby the data relating to the modified energy is modified towards the data relating to the pre-determined parameter.

8 Claims, 4 Drawing Sheets

(51) Int. Cl.
*G01N 29/11* (2006.01)
*G01N 23/16* (2018.01)
*B29C 65/00* (2006.01)
*B29C 70/16* (2006.01)
*B29K 101/12* (2006.01)
*B29K 105/08* (2006.01)
*B29K 307/04* (2006.01)

(52) U.S. Cl.
CPC .......... *G01N 29/11* (2013.01); *B29K 2101/12* (2013.01); *B29K 2105/0872* (2013.01); *B29K 2307/04* (2013.01); *G01N 2223/615* (2013.01); *G01N 2291/0231* (2013.01)

(58) Field of Classification Search
CPC ............. G01N 21/86; G01N 2223/615; G01N 2291/0231; G01N 23/16; G01N 29/11
USPC .......................................................... 156/64
See application file for complete search history.

(56) References Cited

U.S. PATENT DOCUMENTS

2010/0065760 A1    3/2010  Lengsfeld et al.
2014/0316551 A1*  10/2014  Ellis ........................ G01N 27/90
                                                              700/127

\* cited by examiner

METHOD OF MEASURING A PARAMETER OF A COMPOSITE MOULDING MATERIAL

This invention relates to a method for determining a parameter of a multicomponent sheet material and to a method of controlling a process for the manufacture of the multicomponent sheet material, particularly but not exclusively a composite moulding material such as a prepreg material, particularly but not exclusively to such a method which is conducted online. The invention further relates to a method of producing a roll of a multicomponent sheet material selected from a laminate and a pre-impregnated fibre reinforced structure wherein the sheet material has a desired pre-determined parameter, a quality-verified pre-impregnated fibre reinforced structure and to a process controller for controlling a process for the manufacture of a multicomponent sheet material.

Because of their wide applicability, composite materials have found use in a wide range of industries including the automotive, marine and aerospace industries. However, due to their ability to be manufactured in forms suitable for bearing heavy loads, composite materials are especially useful in the design of load bearing structural members, particularly where strength, lightness and ease of shaping may be required. Ensuring reliability in the construction of the sheet material and quality control is imperative.

Composite materials typically include a fibrous material, such as carbon, aramid, glass or quartz, bonded together with a resin material for example an epoxy. The load in such composite materials is carried primarily by the fibrous material, and so, the load carrying properties of the composite can be altered by altering the orientation of the fibres in the composite material. For example, composite materials with unidirectional fibres, such as tapes or tows, may generally exhibit the strongest tensile strength along the axis of the fibres. Woven fabrics and bi-directional mats are typically strongest in the plane of the material. Thus, when designing composite materials, fibre orientation and the number of layers, also known as plies, is typically specified in consideration of the anticipated load the composite item will experience.

Fibre composite laminates or parts may typically be manufactured by first impregnating the fibre reinforcement with resin to form a prepreg, and then consolidating two or more layers of prepreg into a laminate in a so-called "layup" process. Formation of a variety of defects, including wrinkles, voids, delaminations, and the like is inherent in the layup process. For example, voids in the prepreg and/or laminate, may result from the inefficient penetration of the resin into the fibre bundle, tow, or roving, or from outgassing during the consolidation process. Such defects may be formed in greater number when the composite article being formed is relatively large, or incorporates a contour, or otherwise complex shape.

Such defects may not be readily identifiable, detectable or apparent on the surface during the layup process, or, such defects may become visible or exacerbated during the subsequent curing process. The presence of such defects in the finished article may compromise the material strength by as much as a factor of 2, and so, may require that the article be repaired, or, may even require that the part be scrapped, thus contributing to an increase in manufacturing cost due to either the repair cost and/or lead-time required to replace scrapped articles.

A wide range of inspection methods have been applied independently to composite materials. However, the resolution of defects when using some of these composite materials may be limited in some applications. For example, in composite materials wherein the fibres or tows have a random orientation, or in composite materials wherein the fibres desirably comprise carbon, either the structure or the carbon may scatter the measured energy. Further, in many applications, it may be desirable, or even necessary, to obtain multiple measurements, including both measurements of physical parameters and material properties, of the composite material. Many inspection apparatus' are capable of providing only one measurement, or one type of measurement, or provide data with a standard deviation unacceptable in some applications. In some cases, equipment capable of conducting more sophisticated measurements can be expensive and thus not cost-effective in applications where the profit margin of the article being manufactured does not warrant the expense.

A procedure known as the water pickup test for determining the degree of impregnation of a unidirectional prepreg material is known. For this purpose, a specimen of unidirectional prepreg material is initially weighed and clamped between two plates in such a way that a strip of specimen, typically about 5 mm wide protrudes. This arrangement is suspended in the direction of the fibres in a water bath for 5 minutes at room temperature (21° C.). After removing the plates, the specimen is again weighed. The difference in weight is used as a measured value for the degree of impregnation. The smaller the amount of water picked up, the higher the degree of waterproofing or impregnation.

A disadvantage of the water pickup test is that it does not allow any conclusions to be drawn for example concerning the resin distribution in the prepreg material or the surface finish of the prepreg material. The water pickup test procedure merely provides information of an overall bulk effect, it not being possible to differentiate between the individual influencing variables or characteristic parameters. Also, it does not provide a direct measure of fiber areal weight (weight of the fibers per $m^2$) and resin areal weight (weight of the resin per $m^2$).

Furthermore the water pickup test is typically employed off-line as a quality control measure on samples of a material. This necessarily means that a local failure in quality may not be identified or, if it is, a large quantity of material may be deemed to fail the test and lead to wastage.

Fiber areal weight (FAW) and resin areal weight (RAW) are conventionally measured by weighing a composite sample and then subsequently chemically removing the resin from the sample and weighing again. The difference in weight for the sample defines the resin weight content and subtracting the weight of the resin from the initial weight content defines the fiber weight of the sample. Dividing fiber weight and resin weight by the surface area of the sample then results in FAW and RAW. Commonly, the measurement of FAW and RAW is carried out in accordance with ASTM standard D3529. The measurement is laborious, time consuming and therefore inefficient.

The present invention aims to obviate or at least mitigate the above described problems and/or to provide improvements generally.

In addition, a need exists for an improved method of measuring primary parameters of a composite material including fiber and resin content in composite moulding materials.

According to the invention, there is provided a method and a product as herein described and/or as defined in any one of the accompanying claims.

In a first aspect, there is provided a method of determining composite material parameters including fiber volume fraction (FVF) and resin volume fraction (RVF) comprising:
a calibration step:
a) Providing a multimodal radiation source having a least two modes of electromagnetic energy such as radiation
b) Providing means for measuring first and second electromagnetic energy absorption data of a composite material sample exposed to the respective first mode of electromagnetic energy followed by the second mode of electromagnetic energy;
c) Cross correlating the radiation absorption data sets to determine first and second absorption parameters a1 and a2
d) Conducting an analytical determination of FVF and RVF of said composite material defined as Fa and Ra
e) Correlating the first and second absorption parameters a1 and a2 with the determined FVF and RVF by means of a correlating function C
followed by
a determination step:
f) measuring further first and second electromagnetic energy absorption data of a further composite material sample;
g) Cross correlating the electromagnetic energy absorption data sets to determine further first and second absorption parameters b1 and b2
h) Calculating FVF and RVF for the further sample by application of the correlating function C to the further first and second absorption parameters b1 and b2.

In another aspect of the invention in step e) the correlating function C is defined such that the correlated values for FVF and RVF defined as Fc and Rc are such that /Fa–Fc/<4% and /Ra–Rc/<4%, preferably /Fa–Fc/<2% and /Ra–Rc/<2%, more preferably /Fa–Fc/<1% and /Ra–Rc/<1%, or more preferably /Fa–Fc/<0.5% and /Ra–Rc/<0.5%, or /Fa–Fc/<0.1% and /Ra–Rc/<0.1% and/or combinations of the aforesaid ranges.

In this way, there is provided a method which allows accurate measurement of FVF and RVF.

FAW and RAW may be calculated by multiplying the mass of the prepreg with the respective FVF and RVF values and dividing this by the surface area of the prepreg. The determination of FAW and RAW based on FVF and RVF may be conducted as part of the method of the invention. For this purpose the mass and surface area of the prepreg may be determined. RAW and FAW may be expressed as the actual respective fiber and resin weight or they may be expressed as a weight % as defined in ASTM standard D3529.

The method no longer requires laborious standardized tests for measuring FVF, RVF or FAW and RAW in accordance with ASTM standard D3529 for routine testing, particularly in a production environment. Also the measurements can be taken offline or online during or after the production and/or curing of the composite material.

The electromagnetic energy may comprise electromagnetic radiation, preferably x-ray radiation. The energy may be provided by a suitable source.

In another aspect, the invention provides a method of controlling a process for the manufacture of a multicomponent sheet material having a desired pre-determined parameter comprising applying an electromagnetic energy to interact with the sheet material whereby the interaction modifies the applied energy, detecting the modified energy, comparing the modified energy or data derived from it with data relating to the pre-determined parameter and modifying at least one step of the process whereby the data relating to the modified energy is modified towards the data relating to the pre-determined parameter.

In referring to a "parameter" herein, this term is intended to include any aspect of the multicomponent sheet material including its properties.

Any source of radiation may be provided such as acoustic radiation, ultrasound radiation, light radiation, nuclear radiation, ionizing radiation, atomic radiation and/or combination thereof.

The electromagnetic energy may preferably comprise x-ray energy. The electromagnetic energy may comprise energy having a wave length ranging from $0.1 \times 10^{-9}$ to $10 \times 10^{-9}$ m (0.1 to 10 nm) and an x-ray energy between 1 and 50 keV, with a current set to achieve an appropriate contrast, preferably the x-ray energy is between 2 and 35 keV, more preferably between 25 keV at 100 μA to 35 keV at 100 μA, more preferably 25 keV at 120 μA to 35 keV at 120 μA, and more preferably between 20 keV at 100 μA to 30 keV at 100 μA and/or combinations of the aforesaid energies.

In another embodiment the radiation comprises acoustic radiation in the ultrasound range. The ultrasound signal may have a frequency of from 100 kHz to 5 MHz, preferably of from 200 kHz to 1 MHz and most preferably of from 300 kHz to 550 kHz.

The electromagnetic radiation may comprise a microwave signal (wave length ranging from $0.05 \times 10\text{-}2$ to $1 \times 10\text{-}2$ m), an x-ray signal (wavelength 0.01 nm to 10 nm), a light signal (10 nm to 700 nm), an infrared signal (wavelength 700 nm to 0.1 cm) and/or combinations of the aforesaid signals.

In a further embodiment of the invention, multimodal radiation has a first mode which differs from a further mode in at least one radiation property by a value of at least 5%, or 10% or 15% or 20% or 25% or 30% and/or by a value of at most 95%, or 90%, or 85%, or 80%, or 75% or 70%, or 65% and/or by combinations of any of the aforesaid minimum and maximum percentage differences such as a difference in the range of from 5% to 95%, or a difference in the range of from 20% to 65%, etcetera. Preferably, the multimodal radiation has a first mode which differs from a further mode in at least one radiation property by a value of at least 5%, or 10% or 15% or 20% or 25% or 30% or 35% or 40%.

The radiation property may be selected from radiation energy, frequency, phase, wavelength, temperature, bandwidth or width, attenuation, signal to noise ratio, or cross-sectional area.

Suitably the method comprises conducting at least one step of a prepreg and/or laminate manufacturing process and measuring at least two properties of the prepreg and/or laminate before, during or after the at least one step.

Advantageously, the in-line method of the invention allows defects to be detected and compensated for during the manufacture of prepregs and composite materials. This reduces or eliminates the amount of rework or scrap produced in conventional manufacturing processes.

Suitably the process is a continuous process.

The multicomponent sheet material is preferably selected from a laminate and a pre-impregnated fibre reinforced structure. Suitably, the laminate or pre-impregnated fibre reinforced structure is produced in a process comprising an impregnation step comprising contacting a resin with a reinforcement material and one or more further steps selected from a compaction step, a lamination step, a consolidation step and a curing step and wherein at least one step of the process is modified during the process in response to the comparison of the detected x-ray energy with the data relating to the pre-determined parameter.

Suitably, the at least one step of the process is modified continuously during the process thereby to provide in-line feedback control. In the process, any one or more of the process parameters may be modified so as to modify the actual value of the pre-determined parameter towards the desired pre-determined parameter and is suitably selected from the compression of rollers, the gap between resin coater and fibrous material, the temperature of the resin and the flow rate of resin. The method of control using continuous x-ray measurement allows for ongoing quality control of the product being manufactured.

In a preferred embodiment, the process is a continuous process and comprises contacting a resin dispensed from an applicator with a reinforcement material and passing the material between compression rollers wherein the at least one step of the process which is modified in response to the detected x-ray energy is selected from the compression of rollers, the distance between the resin applicator and the reinforcement material, the temperature of resin, the flow rate of the resin and the line speed of the process.

Preferably, the x-ray energy is employed to provide data relating to two or more parameters of the sheet material such as FAW and RAW or FVF and RVF. In a preferred embodiment, the transmittance of the x-ray energy through the thickness of the sheet is measured to determine a first parameter of the sheet and optionally a second parameter of the sheet. Preferably the first and second parameters are selected from the level of resin impregnation of the sheet or RAW, the thickness of the sheet, porosity or void content, particle distribution, or particle concentration.

The process is suitably controlled based on data derived from the x-ray measurement and comparing data relating to the parameter being measured with data relating to a pre-determined value of that parameter. Preferably, the line speed of the process is modified in response to a comparison of the data derived from the detected x-ray energy and data relating to a pre-determined parameter which correlates with a pre-determined level of level of impregnation of the sheet and/or the thickness of the sheet. By modifying the line speed, the level of resin applied per unit area may be controlled and modified to provide the desired pre-determined level of resin in the prepreg.

The property and/or parameter measured can be any that provides useful information about the prepreg and/or laminate. In some embodiments, the measured property and/or parameter provides information related to the properties of the prepreg and/or laminate, while in others, the measured property and/or parameter provide information related to defects, for example voids, cracks, foreign inclusions, delaminations, porosity, wrinkles, or fibre misalignment within the prepreg and/or laminate. Desirably, at least two measurements are made so that more information is obtained as compared to methods of inline inspection of prepregs and/or laminates that utilize only one measurement.

Where two or more measurements are taken, the measurements may be the same measurement, made at different stages of the manufacturing process, while in others, the measurements may be different, and made at the same, or different, stages of the manufacturing process. One measurement may comprise one made substantially at, or in relation to, the surface of the prepreg and/or laminate, while the other measurement may be made below the surface, for example in relation to the subsurface of the prepreg and/or laminate.

The invention enables a quantity of multicomponent sheet material to be produced wherein the quality of the product meets the desired criteria for quality. The continuous process is typically employed to produce a roll of product. Ensuring the roll of product meets the relevant quality criteria reduces waste and is especially important where the product is to be used in applications involving the material bearing high loads.

In a second aspect, the invention provides a method of producing a roll of a multicomponent sheet material selected from a laminate and a pre-impregnated fibre reinforced structure wherein the sheet material has throughout the roll one or more desired pre-determined parameters which lie within a tolerance band around the desired pre-determined parameters by controlling the process for the manufacture of the multicomponent sheet material using a method according to the first aspect of the invention.

Suitably, the tolerance band is not more than 10%, preferably not more than 5% and desirably not more than 1% either below or above the desired pre-determined parameter depending on the particular parameter, the intended end-use and the overall desired quality specification. Whilst the tolerance band may be centred on the desired parameter such that the tolerance band extends equally above and below the desired pre-determined parameter, it is also within the scope of the invention to have a lesser or greater tolerance on one side of the desired pre-determined parameter than the other.

Suitably, the desired pre-determined parameters are selected from FAW and RAW.

In a further aspect, the invention provides a pre-impregnated fibre reinforced structure comprising a roll of a multicomponent sheet material selected from a laminate and a pre-impregnated fibre reinforced structure wherein at least one parameter of the multicomponent sheet material has been altered during production of the roll in response to data obtained from x-ray measurements carried out during the production of the multicomponent sheet material.

Suitably the pre-impregnated fibre reinforced structure comprising a roll of a multicomponent sheet material selected from a laminate and a pre-impregnated fibre reinforced structure has been obtained by a method according to the second aspect of the invention.

Advantageously, the pre-impregnated fibre reinforced structure need not be subjected to off-line quality control analysis. If however, this is desired as a complementary quality control measure, the pre-impregnated fibre reinforced structure may be subjected to a known quality control process in addition to the x-ray method of the present invention.

The invention also provides a method of controlling a process for the manufacture of a multicomponent sheet material having a desired pre-determined parameter comprising applying an x-ray energy to interact with the sheet material whereby the interaction modifies the x-ray energy, detecting the modified x-ray energy, comparing the modified x-ray energy or data derived from it with data relating to the pre-determined parameter and modifying at least one step of the process whereby the data relating to the modified x-ray energy is modified towards the data relating to the pre-determined parameter and wherein the multicomponent sheet material is subjected to standardized tests for measuring RAW and FAW in accordance with ASTM D 3529.

The present invention may be employed in combination with other quality control methods Any additional methods may be selected based upon the parameter or property(ies) being measured. Additional measurement methods include imaging techniques, such as acoustic holography, optical metrology and many varieties of cameras, for example microwave cameras, for dimensional measurements, such as length, width, depth, or measurements made in more than one dimension; thermometers or thermocouples for the measurement of thermal conductivity; magnetometers such as hall-effect sensors, giant magneto-resistive sensors, anisotropic magneto-resistive sensors, atomic magnetometers, superconducting quantum interference devices (SQUIDS) or eddy current coils for the measurement of magnetic permeability; capacitive plates or striplines for the measurement of dielectric constant; ohmmeters and eddy current coils for the measurement of electric conductivity; densitometers or x-ray for the measurement of density or porosity; and magnetometers and coils for the measurement of nuclear quadruple resonance frequency.

In some embodiments, at least one of the measurements suitably provides information related to a property of the prepreg or laminate, or the presence of a defect in the same. For example, at least one measurement may desirably provide information related to the thermal conductivity, magnetic permeability, dielectric constant, electric conductivity, density, nuclear quadruple resonance frequency, etc., of the prepreg and/or laminate. In some embodiments, x-ray measurements are employed and provide information related to the porosity, fibre volume fraction, voids and/or delaminations of the prepreg and/or laminate.

The present invention may be employed in combination with the method described in US2010/0065760 for determining at least one characteristic parameter of a CRP specimen, in particular a specimen of prepreg material for aerospace, comprising the following method steps: presenting the specimen, irradiating the specimen with a predetermined spectrum of electromagnetic radiation, recording the interaction between the specimen and the electromagnetic radiation in a data record and determining the characteristic parameter from the recorded data record.

In a further aspect, the invention provides a method of calibrating an x-ray apparatus for use in a method of controlling a process for the manufacture of a multicomponent sheet material having a desired pre-determined parameter comprising manufacturing a multicomponent sheet material applying an x-ray energy to interact with the sheet material during its production, detecting the x-ray energy after interaction with the sheet material, analysing one or more parameters of the sheet material by a water pick-up method and correlating the detected x-ray energies with the results of the water pick-up method thereby to calibrate the detected x-ray results with the one or more parameters of the sheet material.

In another aspect, there is provided an apparatus for the manufacture of a prepreg and/or laminate. The apparatus comprises a controller, a resin infusion apparatus, at least one measurement apparatus, and a processor. The processor is operatively disposed relative to the measurement apparatus and controller so that information may be transmitted therebetween. Suitably the method of the invention is controlled using a process controller.

In a further aspect, the invention provides a process controller for controlling a process for the manufacture of a multicomponent sheet material having a desired pre-determined parameter which comprises contacting a resin dispensed from an applicator with a reinforcement material and passing the material between compression rollers and applying an x-ray energy to interact with the sheet material whereby the interaction modifies the x-ray energy, detecting the modified x-ray energy, comparing the modified x-ray energy or data derived from it with data relating to the pre-determined parameter and modifying at least one step of the process, the controller comprising:

i) a process parameter controller for controlling one or more the parameters in the process selected from the level of force exerted by the compression rollers, the distance between the resin applicator and the reinforcement material, the temperature of the resin, the flow rate of the resin and the line speed of the process;

ii) a comparator for comparing the detected x-ray energy or data derived from it with data relating to the desired pre-determined parameter;

iii) a parameter modifier for receiving data from the comparator and providing an energy to the process parameter to modify at least one of the parameters in the process whereby the actual value of the pre-determined parameter approaches the desired value of pre-determined parameter.

In a preferred embodiment, the line speed of the process is controlled in response to measured x-ray energy.

In a further aspect, the invention provides a production line for producing a roll of a multicomponent sheet material comprising impregnation apparatus for contacting a resin with a reinforcement material and one or more further apparatus selected from compaction apparatus, lamination apparatus, consolidation apparatus and curing apparatus and x-ray apparatus adapted to apply x-ray to the sheet and to detect an x-ray energy and a process controller according to the invention Suitably the absorption is correlated with a calibration model derived from measurements obtained using conventional methods for measuring FAW and RAW.

The invention also provides for articles prepared from prepregs and/or laminates made using the method of the invention.

In some embodiments dimensional information, such as length, width, depth, or measurements made in more than one dimension is suitably obtained. Many imaging techniques are available capable of providing such measurements, either directly, or indirectly via an image that may be further analyzed to provide the desired dimensional information. Examples of such imaging techniques include acoustic holography, eddy current array imaging, optical metrology and many varieties of cameras, for example microwave cameras.

In some embodiments, optical metrology may be used in addition to x-ray and is advantageously capable of providing information related to wrinkles or waviness present in the reinforcement material, prepreg and/or laminate. Techniques for conducting optical metrology measurements, as well as analyzing the results thereof, are well known to those of ordinary skill in the art, and are described generally in Yoshizawa, Taoru, Handbook of optical metrology principals and applications, Taylor & Francis, Boca Raton, co. 2008 hereby incorporated by reference herein in its entirety. Further, equipment for conducting such measurements is commercially available from a variety of sources including General Electric Company, FARO and Minolta.

In a preferred embodiment, x-ray measurements are advantageously taken during infusion, and/or prior to, or during compaction, when they are expected to provide information related to the porosity of the prepreg. Suitably an x-ray probe(s) is employed and may be placed in close proximity to the resin infusion stage and/or the compression/compaction stage, where it will collect data indicative of the porosity of the prepreg/laminate at a given depth.

The data is then processed by the processor to provide data, for example indicative of the effect of any defects in the green state prepreg and/or laminate on the number and severity of defects the corresponding cured part and/or the impact of any such defects on cured part strength. The processed data provided to the controller, which may then adjust parameters of the process, if desired or required, to reduce the amount, or magnitude, of defects generated in the prepreg and/or laminate by the process.

Process adjustments that may impact the presence, number or impact of defects in the green state prepreg and/or laminate include, but are not limited to, tow tension, temperatures, layup speed, roller pressure, and resin content. And, the processed data may indicate, and so the controller may adjust any of these manually or automatically. Automatic control may be advantageous in some embodiments, as it provides the opportunity for a closed-loop process.

The apparatus employed for putting the invention into effect suitably comprises appropriate sensors, or arrays of sensors, operatively disposed relative to the prepreg and or laminate, or processing equipment at the point of the manufacturing process at which the measurement information is desirably obtained. In some embodiments, the sensor or array(s) of sensors may advantageously be placed proximal to, distal to, or in close proximity to where the resin is desirably infused into the reinforcement material, and/or compaction/compression of the prepreg, layup of one or more prepregs to provide the laminate, or consolidation of the laminate takes place. Stated another way, at least one of the measurements is taken before, during or after infusion of a resin onto a reinforcement material, a compaction step, a lamination/layup step, a consolidation step and/or a curing step.

In a preferred embodiment the x-ray transmitter or source and receiver are located above and beneath the sheet material. Preferably the transmitter and receiver do not contact the sheet material. The energy may also be transmitted or absorbed through the thickness of the sheet or prepreg. Absorption of the energy (as measured by the difference between the energy of the transmitted energy and the received energy following transmission through the prepreg or sheet) provides a measurement of one or more parameters of the sheet or prepreg.

The phase difference between the original transmitted energy and received energy may also be indicative of certain properties of the prepreg or sheet such as porosity or surface defects.

Sensing circuits necessary for operation of x-ray sensor elements can be prone to electromagnetic (EM) interference. Therefore it is necessary to keep the wires of the sensor circuit short. It is preferable that the sensing circuit and the necessary electronics for receiving an input from the sensors should be located in close proximity to the sensor, and insulated from EM radiation. Preferably this will be within 7 m of the sensor, preferably still, mounted on the same sliding track or gantry as the sensor elements. Preferably the electronic systems not associated with the sensing circuit (e.g. the power supply) are insulated to prevent EM interference affecting the sensing circuit. Preferably all of the electronics associated with the transmitter and sensor elements are housed in EM insulated compartments, with the sensing circuit in a separate compartment.

An undesirable by-product of the handling of carbon fibres is the production of conductive airborne particles which can disrupt electrical components. It is therefore preferable that all electrical components of the present invention are housed in positive pressure environments to prevent the ingress of airborne conductive particles to prevent damage.

In those embodiments wherein optical metrology is employed to obtain one of the measurements, it may advantageously be employed during layup, when it is expected to provide information related to the laminate surface topography.

Suitably, the data obtained from at least one measurement is advantageously used to monitor and/or modify the manufacturing process. In other words, the data obtained from the measurements may be provided to a processor capable of manipulating the data. For example, the data may be manipulated to provide a historical overview of the measured property of the prepreg and/or laminate, or, the data may be manipulated in order to predict how the properties and/or defects within prepreg and/or laminate may develop during further processing and/or storage.

In some embodiments, the data may be manipulated in order to predict how defects in the uncured, or "green-state", prepreg and/or laminate may present in the cured part. In the same, or other embodiments, the data may be manipulated in order to correlate any defects detected in the measuring steps to cured part strength. In other words, the data may be manipulated in more than one way, to provide more than one indication. In some embodiments, for example, the data may be manipulated to provide both a prediction of how defects in green-state parts will present in cured parts, and what impact these defects will have in the cured part strength.

Process modelling software and techniques are known in the art, and these may also be applied to the data obtained during practice of the methods to predict, for example defects that may remain, or be exacerbated in a cured part from green state indications, and the impact any such defects may have on the cured part strength. For example, suitable methods for conducting such analysis are described, for example, in Sridhar Ranganathan, Suresh G. Advani, and Mark A. Lamontia, "A Non-Isothermal Process Model for Consolidation and Void Reduction during In-Situ Tow Placement of Thermoplastic Composites," Journal of Composite Materials, 1995 vol. 29, pp. 1040-1062; Yerramalli, C. S., Waas, A. M., "A nondimensional number to classify composite compressive failure," Journal of Applied Mechanics, Transactions ASME, 2004, vol. 71, no. 3, pp. 402-408 and Yerramalli, C. S., Waas, A. M., "A failure criterion for fibre reinforced polymer composites under combined compression-torsion loading", International Journal of Solids and Structures, 2003, vol. 40, no. 5, pp. 1139-1164, hereby incorporated herein by reference for any and all purposes.

Such analysis can be used, in some embodiments, to make changes to the process in order to minimize, or even eliminate, defect formation. Such embodiments thus provide the advantage of a reduction in reworking, or scrap, of defective articles made by the process. Such process modifications may either be made manually, or via an automated controller operatively disposed relative to the processor in order to receive information therefrom, and relative to the prepreg and/or layup apparatus, in order to provide information thereto.

The present methods are advantageously and readily incorporated into any apparatus for the manufacture of a prepreg and/or laminate, and so, such apparatus are also provided herein. Generally speaking, the apparatus comprises a controller, a resin infusion apparatus, at least one measurement apparatus, and a processor. The processor is operatively disposed relative to the measurement apparatus and controller so that information may be transmitted therebetween. In some embodiments, the apparatus may also comprise a layup apparatus.

The at least one measurement apparatus may be positioned at any location wherein data related to the prepreg and/or laminate can be, and is desirably, collected. In some embodiments, the same type of measurement apparatus may be used at more than one location, while in the same, or in other, embodiments, at least two measurement apparatus are utilized. The measurement apparatus will depend upon the data desirably obtained, and can be chosen based upon the same. In some embodiments, an optical metrology unit is utilized in combination with an x-ray measurement device.

For example, in those embodiments, wherein at least one measurement provides dimensional data, and the measurement is taken with one or more optical metrology device, the device(s) may be positioned, for example in close proximity to the layup head, and where it will generate 2-D images of the laminate surface topography that, in turn, can be analyzed to detect and characterize any wrinkles in the surface of the laminate.

The present methods and apparatus may be utilized in connection with the manufacture of any prepreg and/or laminate, regardless of the composition thereof. Prepregs typically comprise one or more curable resins, and one or more reinforcing materials, while laminates typically comprise multiple prepregs, layered one upon another.

Generally speaking, suitable curable resins for use in prepregs and laminates include thermoplastic polymeric compositions such as polystyrene, polyethylene terephthalate, polymethylmethacrylate, polyethylene, polypropylene, polyvinylacetate, polyamide, polyvinyl chloride, polyacrylonitrile, polyesters, polyvinyl chloride, polyethylene naphthalate, polyether ketone, polysulfone, polycarbonate, and copolymers thereof.

Prepregs and laminates may also utilize thermoset resins, suitable examples of which include, but are not limited to epoxies, polyesters, vinylesters, phenolic resins, polyurethanes, polyamides, or combinations of two or more of these. Adhesive compositions particularly well suited for use in the present invention include crosslinked thermosetting systems such as polyesters, vinyl-esters epoxies (including acid, base and addition cured epoxies), polyurethanes, silicone resins, acrylate polymers, polysiloxanes, polyorganosiloxanes, and phenolics, as well as blends or hybrids of any of these.

Structural adhesives are often used in prepregs and laminates, and may be used in the prepregs and laminates prepared by the present methods and/or apparatus. Preferred structural adhesives for use in the present composite systems include polyesters, methyl methacrylates, and the like.

Any suitable reinforcing material may be infused using the apparatus, systems and methods described. For example, relatively continuous fibres, or tows, may be arranged to form a unidirectional array of fibres, a cross-plied array of fibres, or bundled in tows that are arranged to form a unidirectional array of tows, or that are woven or cross-plied to form a two-dimensional array, or that are woven or braided to form a three-dimensional fabric. For three-dimensional fabrics, sets of unidirectional tows may, for example, be interwoven transverse to each other.

Useful fibres to be included in such reinforcing materials, such as tapes or fabrics, include without limitation, glass fibres, carbon and graphite fibres, basalt fibres, polymeric fibres, including aramid fibres, boron filaments, ceramic fibres, metal fibres, asbestos fibres, beryllium fibres, silica fibres, silicon carbide fibres, and the like. The fibres may be non-conductive or conductive, depending upon the desired application of the prepreg.

The present methods may be applied in the manufacture of any article comprising a prepreg and/or laminate and are particularly advantageous when applied to large articles due to the cost associated with the manufacture of such articles, and thus, the cost of reworking or scrapping the same. The present methods may also provide particular benefit when applied to prepregs, laminates and/or articles comprising these wherein the reinforcement material comprises carbon filaments or fibres. Carbon has a significantly higher stiffness and lower mass than many other reinforcement materials, for example glass composites. Thus, its use as a reinforcement material can enable the manufacture of prepregs, laminates and articles that may be larger, and yet lighter, with yet acceptable strength for the desired application. However, the final strength of components made of prepregs and/or laminates comprising carbon can depend greatly on the manufacturing process. Defects such as wrinkles, delaminations, porosity and voids can greatly reduce the final strength of the composite by introducing stress concentrators into the material structure that may cause localized premature failure or redirect stresses from applied loads in ways that are not accounted for in the design of the component.

Examples of industries wherein large scale articles are routinely manufactured from prepregs and/or laminates, and/or prepregs and/or laminates comprising a carbon containing reinforcement material include the energy industry, where large segments of, for example pipeline or other plant apparatus, may find benefit from application of the principles discussed herein. Examples of particular applications further include wind turbine components, such as, turbine blades or subcomponents of such, for example spars, spar caps, airfoil skins, or the cylindrical root section or tower sections of wind turbines. Laminates prepared from prepregs prepared using the methods and apparatus described may also be used in aviation applications, such as wing skins, fuselage skins, spars, or flat laminates such as ribs.

The invention is illustrated with reference to the accompanying drawings in which.

Figure 1:
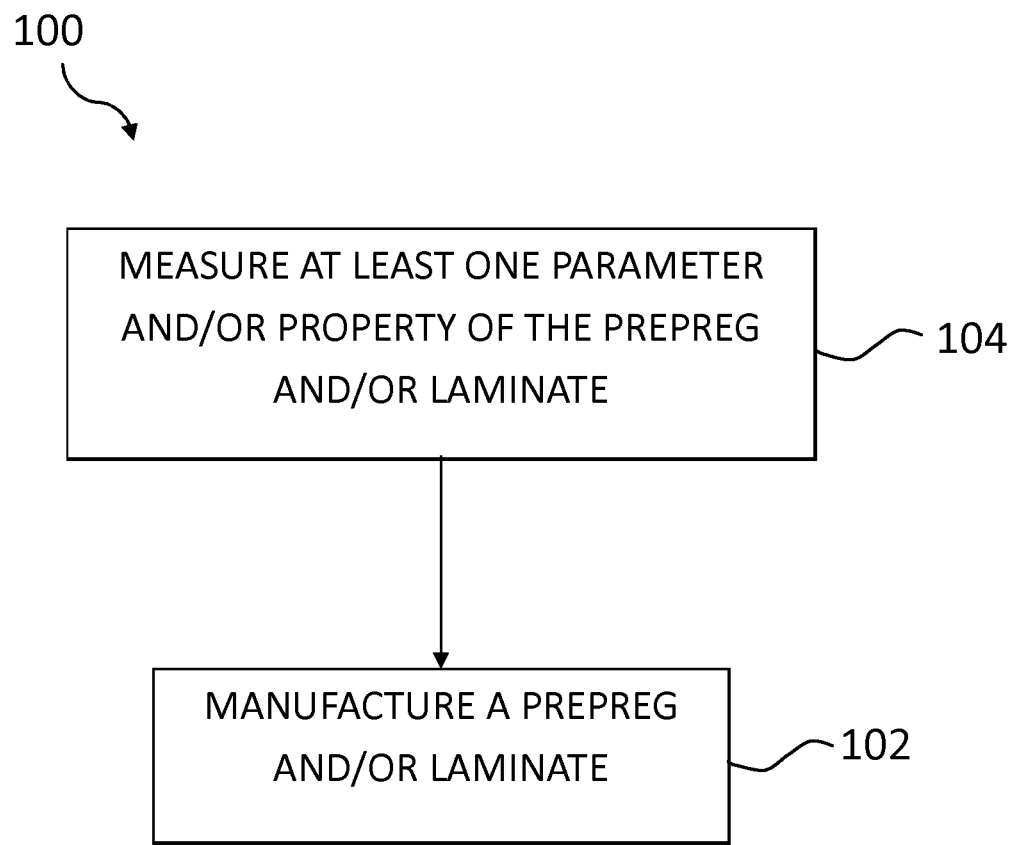
FIG. 1 is a flow chart representing steps in an inline inspection method in accordance with some embodiments of the invention.

FIG. 1 is a flow chart illustrating one embodiment of the method. As shown, method 100 involves manufacturing a prepreg and/or laminate at step 102, and measuring a parameter or property of the prepreg and/or laminate using an x-ray method during the manufacture thereof at step 104. The measurements may generally be taken at any point in the manufacturing process of a prepreg or laminate including, resin infusion, compression/compaction, lamination/layup, consolidation and curing.

Figure 2:
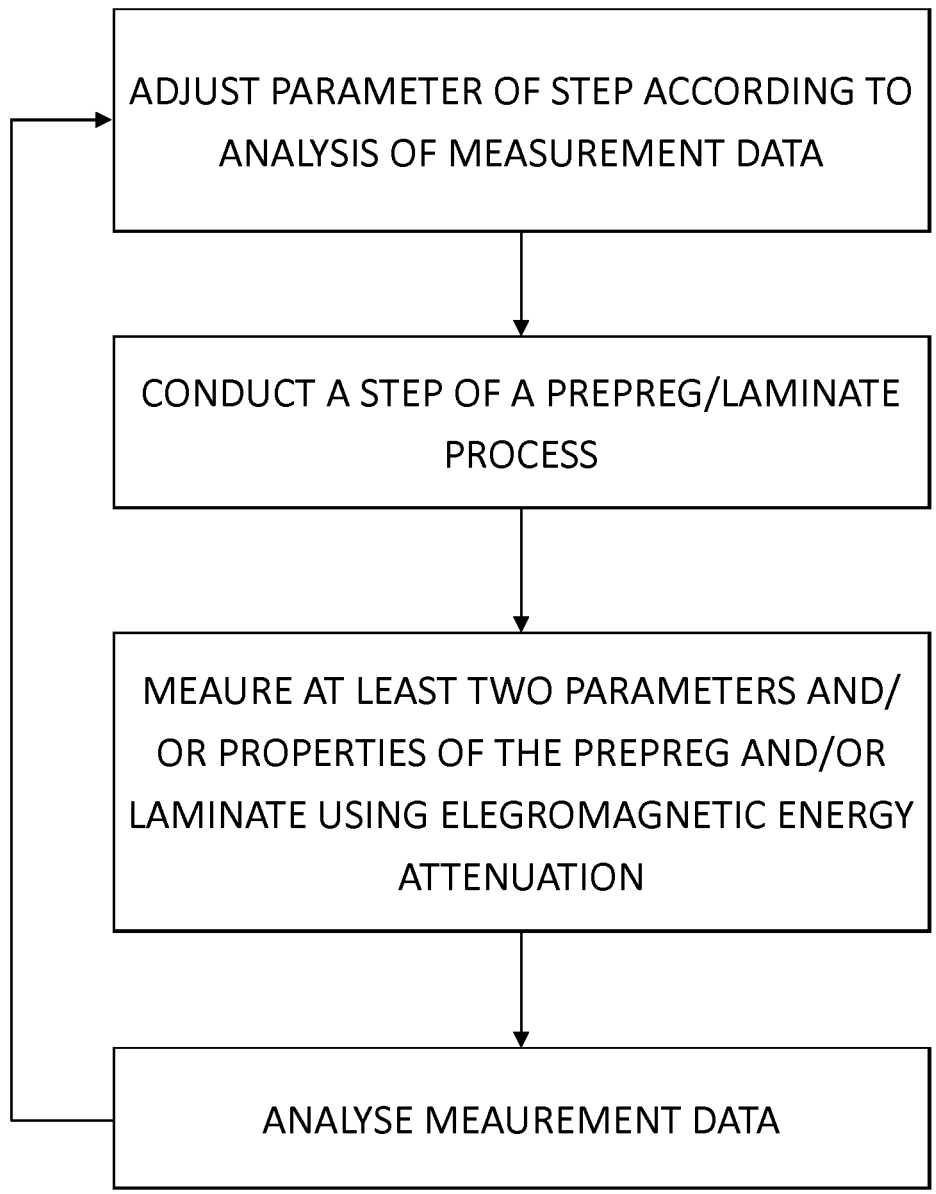
FIG. 2 is a flow chart representing steps in an exemplary inline inspection method in accordance with some embodiments of the invention.

In FIG. 2, method 400 comprises conducting a step of a prepreg/laminate manufacturing process at step 404, measuring at least two properties of the prepreg/laminate at step 406 comprising FAW and RAW, and analyzing the data obtained at step 408. The analysis of the data may then be utilized to adjust the manufacturing process, if necessary or desired, as shown at step 402.

Figure 3:
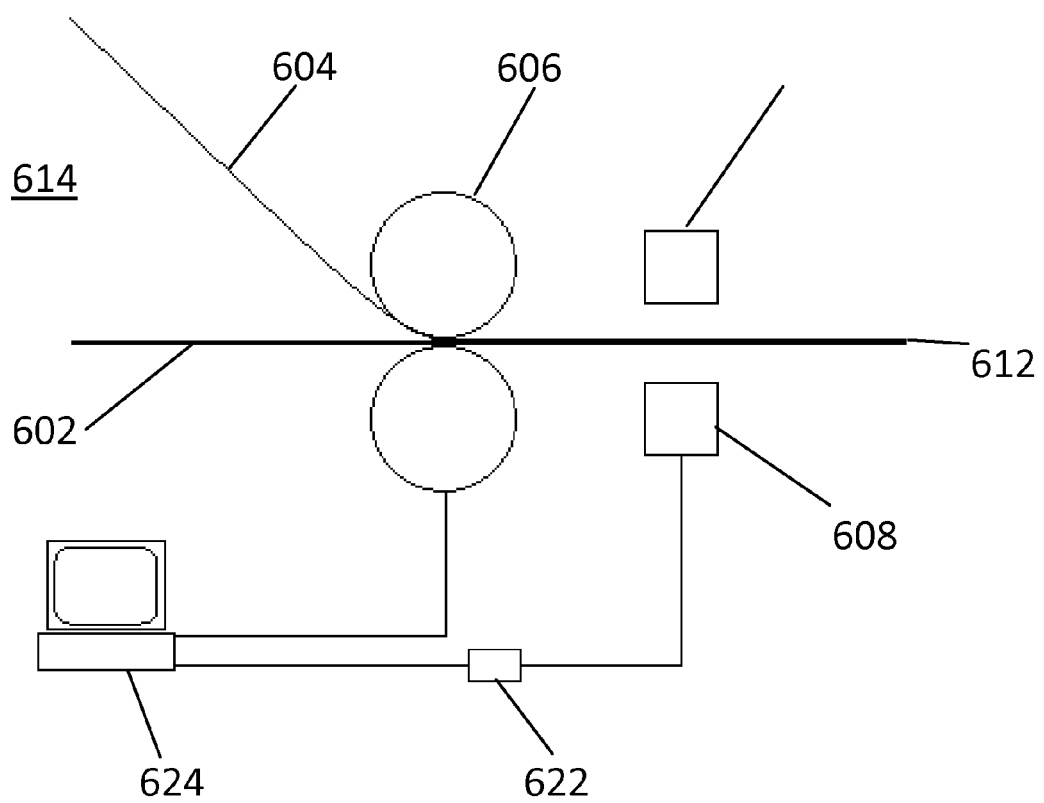
FIG. 3 is a diagram presenting an implementation of the method of the invention according to another embodiment of the invention.

In FIG. 3, an implementation of the method of the invention 614 according to another embodiment is shown. A prepreg and/or laminate material 612 is formed by feeding a reinforcement material 602 through rollers 606 with a film of curable resin 604. A multimodal (at least bimodal) x-ray source 610 is positioned after the rollers and aligned parallel to the width of the prepreg at one side of the prepreg, facing the prepreg sheet. A detector receiver 608 is positioned on the opposite side of the prepreg to the source in a position opposite to the source. The receiver 608 receives the energy which is not absorbed by the prepreg. The output of the receiver 608 which is in the form of a CCD (charge coupled device) having a resolution of 98.2 µm and a size of 100 mm×100 mm as supplied by Computer Information Technology Ltd., is received by an acquisition system 622. A signal processing unit 624 then compares the received response to a reference response for each mode of the x-ray source which corresponds to the response of a calibration sample for each mode. The change of the received response to the reference response is correlated to the impregnation level of the prepreg to provide the FAW and RAW of the prepreg. This can be displayed in real-time. The data is compared to predetermined values and used to adjust a parameter of the manufacturing process (e.g. roller force) with closed loop control, to ensure uniform impregnation of resin into the reinforcement material. The resin thickness data is also recorded to associate this with a corresponding batch of prepreg. This system can also be used to detect errors and fluctuations of resin that occur, for example, following a change of film roll or fibre creel.

Figure 4:
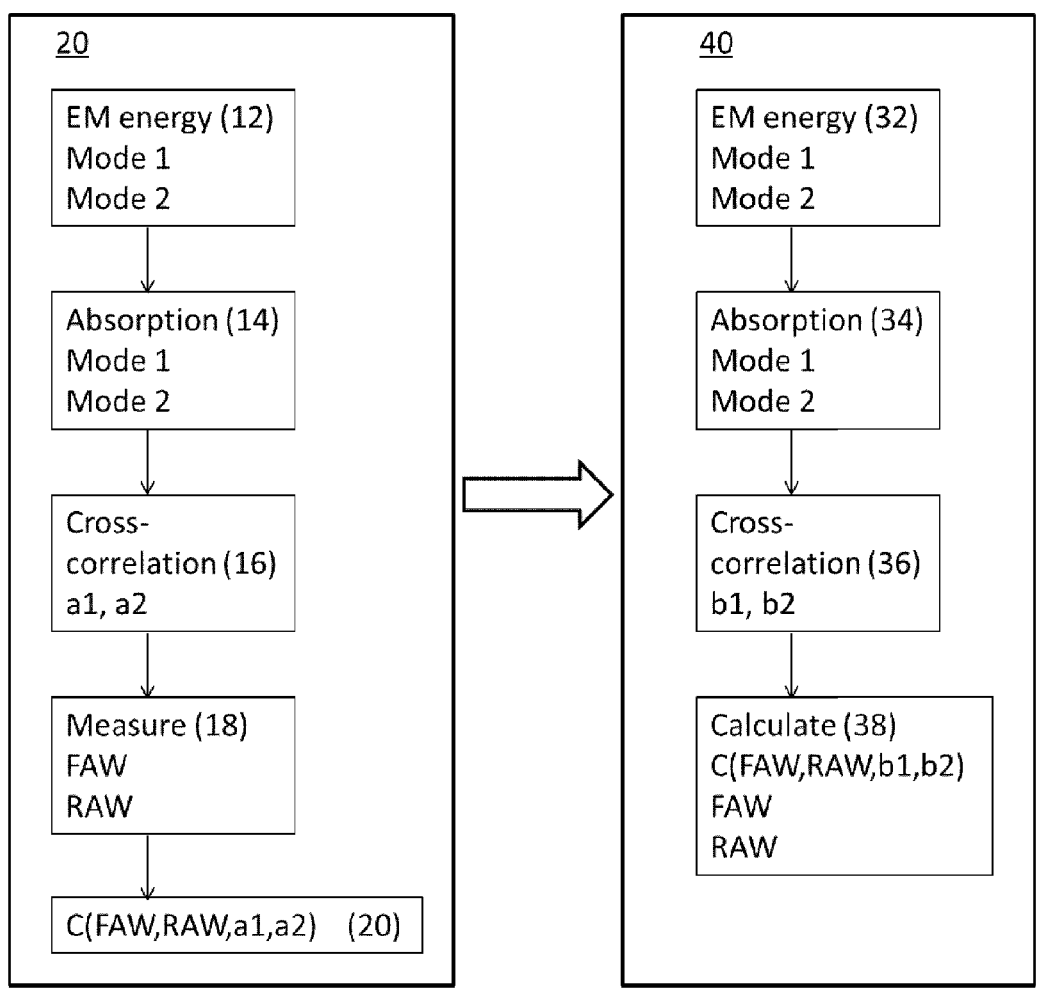
FIG. 4 is a diagram presenting the calibration step and the determination step of the method of the invention.

In FIG. 4, there is shown a method of determining composite material parameters including fiber areal weight (FAW) and resin areal weight (RAW). The method consists of two steps, a calibration step (20) and a measurement step (40). Following the calibration step (20) the measurement step (40) can be repeated over and over.

The calibration step (20) comprises providing a multi-modal radiation source having two modes of x-ray radiation. The radiation source is provided by Beryllium (Be). A first mode of energy is provided by selecting energy values of 20 keV at 100 µA to 25 keV at 120 µA, preferably 25 keV at 100 µA to 25 keV at 120 µA and/or combinations thereof; and a second mode of energy is selected from 30 keV at 100 µA to 35 keV at 120 µA, preferably 35 keV at 100 µA to 35 keV at 120 µA and/or combinations thereof; the preferred modes are 25 keV at 100 µA and 35 keV at 100 µA.

The two modes of the radiation source are applied to the composite material (12) and the absorption for the two modes is measured (14). The two measured modes are cross-correlated (16) which results in two parameters a1 and a2 for each respective mode. The cross-correlation method is for example disclosed in Advanced Signal Processing: Theory and Implementation for Sonar, Radar, and Non-Invasive Medical Diagnostic Systems, Second Edition, 2010.

In addition the fiber areal weight and resin areal weight are measured analytically. This step is preferably carried out in accordance with standard measurement methods as hereinbefore described. The FAW and RAW are then correlated to the parameters a1 and a2 by means of a function C(FAW, RAW,a1,a2) (20). Suitable linear functions C(FAW, RAW, a1,a2) may be FAW=a1*K1 and RAW=a2*K2 where K1 and K2 are constants. Higher order functions may also be defined.

The calibration steps may be repeated several times to increase the accuracy of the function C(FAW, RAW,a1,a2) and to define average constants <K1> and <K2>. The calibration 20 may also be repeated several times for composites having different RAW and FAW compositions to increase the accuracy of the function C(FAW, RAW,a1,a2).

Once the function C(FAW, RAW,a1,a2) has been established, FAW and RAW of a composite can be measured in accordance with the measurement step 40. In this step, the same two modes of energy or radiation are applied to the composite in step 32. The absorption of the energy is measured 34 and the same cross-correlation is conducted to calculated parameters b1 and b2 in step 36.

The FAW and RAW for the composite can then be calculated from the calibration function C(FAW, RAW,b1, b2) in step 38.

In this way, the absorption of radiation energy transmitted energy is correlated to the FAW and RAW and used to reliably measure FAW and RAW in composites. The measurements can be displayed in real-time. The data may also be compared to predetermined values and used to adjust a parameter of the manufacturing process (e.g. roller force) with closed loop control, to ensure uniform impregnation of resin into the reinforcement material.

This method can also be used to detect errors and fluctuations of resin that occur, for example, following a change of film roll or fibre creel.

There is thus provided a method of controlling a resin impregnation process and resin impregnated materials as controlled by such a method. The method may also be used to determine the FAW and RAW in cured composite material, and in particular in composite materials which comprise a fibrous reinforcement material and a resin material. In this way, the quality of resin impregnated materials can be measured.

The invention claimed is:

1. A method of determining composite material parameters comprising fiber areal weight %, fiber volume fraction, resin areal weight % and resin volume fraction comprising:
   A) a calibration step comprising:
      a) providing a multimodal radiation source having a least two modes of electromagnetic energy selected from the group consisting of x-ray radiation, acoustic radiation, ultrasound radiation, light radiation, nuclear radiation, ionizing radiation, atomic radiation and/or combinations thereof;
      b) providing means for measuring first and second electromagnetic energy absorption data of a composite material sample exposed to the respective first mode of electromagnetic energy followed by the second mode of electromagnetic energy;
      c) cross correlating the radiation absorption data sets to determine first and second absorption parameters a1 and a2:
      d) conducting an analytical determination of fiber areal weight % and resin areal weight %, or fiber volume fraction and resin volume fraction, of said composite material defined as Fa and Ra, respectively:
      e) correlating the first and second absorption parameters a1 and a2 with the determined fiber areal weight % and resin areal weight %, or fiber volume fraction and resin volume fraction, by means of a correlating function C;
   B) a determination step comprising:
      a) measuring further first and second electromagnetic energy absorption data of a further composite material sample;
      b) cross correlating the electromagnetic energy absorption data sets to determine further first and second absorption parameters b1 and b2; and
      c) calculating fiber areal weight % and resin areal weight %, or fiber volume fraction and resin volume fraction, for the further sample by application of the correlating function C to the further first and second absorption parameters b1 and b2.

2. A method according to claim 1, wherein in step (A)(e) the correlating function C is defined such that the correlated values for fiber areal weight % and resin areal weight %, or fiber volume fraction and resin volume fraction, defined as Fc and Rc are such that /Fa−Fc/<4% and /Ra−Rc/<4%.

3. A method according to claim 1, wherein the electromagnetic energy comprises x-ray radiation.

4. A method according to claim 3, wherein the electromagnetic energy comprises energy having a wave length ranging from $0.1 \times 10^{-9}$ to $10 \times 10^{-9}$ m (0.1 to 10 nm) and an energy between 20 keV at 100 µA to 25 keV at 120 µA.

5. A method according to claim 1, wherein the method comprises conducting at least one step of a prepreg and/or laminate manufacturing process and measuring at least two properties of the prepreg and/or laminate before, during or after the at least one step.

6. A method according to claim 1, wherein the method is conducted online or inline.

7. A method according to claim 6, wherein the process is modified continuously during the process to provide in-line feedback control of the resin areal weight % and fiber areal weight %, or fiber volume fraction and resin volume fraction, of the composite material.

8. A method according to claim 7, wherein one or more process parameters are adjusted selected from the compression of rollers, the gap between resin coater and fibrous material, the temperature of the resin and the flow rate of resin, line speed and/or a combination of the aforesaid parameters.

* * * * *